United States Patent
Hoffman et al.

(10) Patent No.: US 7,019,830 B2
(45) Date of Patent: Mar. 28, 2006

(54) PROCESS AND APPARATUS FOR QUALITATIVE AND QUANTITATIVE ANALYSIS OF AN ANALYTE

(75) Inventors: Daniel Hoffman, Bonn (DE); Michael Moske, Rheinbach (DE)

(73) Assignee: Stiftung Caesar Ctr-Advanced European Studies & Research, (DE)

( * ) Notice: Subject to any disclaimer, the term of this patent is extended or adjusted under 35 U.S.C. 154(b) by 330 days.

(21) Appl. No.: 10/439,079

(22) Filed: May 15, 2003

(65) Prior Publication Data

US 2003/0214652 A1    Nov. 20, 2003

(30) Foreign Application Priority Data

May 15, 2002  (DE) .............................. 102 21 792

(51) Int. Cl.
*G01J 3/30* (2006.01)

(52) U.S. Cl. .................... 356/317; 356/318; 250/458.1

(58) Field of Classification Search ................ 356/317, 356/318; 436/525, 524; 435/6, 7.1; 250/458.1
See application file for complete search history.

(56) References Cited

U.S. PATENT DOCUMENTS

| 6,263,286 B1 * | 7/2001 | Gilmanshin et al. .......... 702/19 |
| 6,297,018 B1 | 10/2001 | French et al. |
| 2005/0064604 A1 * | 3/2005 | Bohmann et al. ........... 436/525 |

FOREIGN PATENT DOCUMENTS

DE   101 59 579 A1 *  6/2003

* cited by examiner

*Primary Examiner*—Layla G. Lauchman
(74) *Attorney, Agent, or Firm*—Robert W Becker & Associates; Robert W Becker

(57) ABSTRACT

A process for qualitative and quantitative analysis of an analyte in a solution includes irradiating a first chromophore with an electro-magnetic radiation while simultaneously moving an arrangement structure and the analyte relative to one another in a manner which effects extension of the elastic coupling interconnecting the first chromophore and a second chromophore. The process also includes measuring the intensities of a fluorescent light having a respective wavelength $\lambda_1$ and a fluorescent light having a respective wavelength $\lambda_2$ during the movement of the arrangement structure and the analyte relative to one another. The type and the amount of the analyte is determined as a function of the intensities of the fluorescent light having the respective wavelength $\lambda_1$ and the fluorescent light having the respective wavelength $\lambda_2$.

20 Claims, 1 Drawing Sheet

PROCESS AND APPARATUS FOR QUALITATIVE AND QUANTITATIVE ANALYSIS OF AN ANALYTE

BACKGROUND OF THE INVENTION

The present invention relates to a process for qualitative and/or quantitative analysis of an analyte, in particular, an analyte in a biological solution. The present invention concerns, as well, a sensor, which is especially operable for transforming the process.

The purpose of such biosensors is the specific detection of biomolecules. There are a multitude of scientifically and economically important fields in which biosensors can be deployed for this purpose. In this regard, for example, the medical diagnostic field, the environmental diagnostic field, the development of pharmaceutical materials or the monitoring of industrial biotechnology processes come to mind. Particularly noteworthy examples of the scientific and economic significance of biosensors are the GeneChip® offered by Affymetrix® and the therewith deployed products, which find ever-increasing use in academic and industrial research.

The requirements imposed on such biosensors are consequently multi-fold. It is typically desired that such biosensors have a high sensitivity and specificity with respect to small analyte amounts and a high measurement throughput, a high robustness and, frequently, the possibility, as well, for miniaturization and for integration thereof into arrays. Moreover, it is advantageous if the biomolecules to be detected do not need to be marked with fluorophors or with radioactive isotopes, as is conventional.

A widely used, economically successful, type of sensor is based on the effect of Surface Plasmon Resonance (SPR). In this connection, a multitude of measurements can be performed up to and including the characterization of the bonding kinetics of biomolecules. Typically, the protein amounts can be measured down to quantities in the pM range.

Proteins, which only occur in small concentrations, can, therefore, not be detected by these approaches. A variation of the SPR process, which is substantially more sensitive than the above-noted approaches, exploits the fluorescence of the analyte. The disadvantage of this variation is the necessity to mark the analyte with fluorophor.

Fluorophor markings are also necessary in connection with the above-noted GeneChip®, a widely used process with a relatively high integration grade. This process permits an entire genome to be arranged in an array. The sensitivity of this process is increased by amplification of the nucleic acid analytes via the polymerase chain reaction (PCR). The process is consequently very sensitive. In this form, however, the process is limited to the nucleic acids as the analytes. In connection with the use of electro-chemical sensors, further material must typically be added to the actual analyte. The reactions of the added further material leads to the release, as a function of the concentration of the actual molecule of interest in the analyte, of electrical charge carriers, which are detected as current. In another configuration, there is additionally detected, via the use of the capacitative measurement process, the di-electric property changes of the measurement system, or impedance spectroscopy is deployed.

A further widely used sensor type is the quartz micro balance or scale, which has the important advantage of a compact construction in comparison to the SPR systems. The Surface Acoustic Wave (SAW) micro balance or scale is comparable in its sensitivity with the SPR sensors and the SAW micro balance or scale is most commonly deployed for measurements in the gas phase. In the liquid phase, which is more relevant for many inquiries of interest, detection via the SAW sensors suffers due to the strong damping exerted by the liquid.

Mass spectrometry processes, such as Surface Enhanced Desorption/Ionization (SELDI), can, in fact, be performed without markings on the analytes and the sensitivity of such processes is sufficient under favorable conditions for measurements into the attomol range. On the other hand, the hardware effort is comparatively high, the heretofore possible integration grade is still low, and a quantification of the analyte is difficult.

In connection with the conventional state of the art, several biosensor types are known. In practice, it has, however, heretofore not been possible to develop a biosensor which simultaneously and substantially satisfies all of the above-noted analyte measurement requirements.

SUMMARY OF THE INVENTION

The present invention provides a solution to the challenge of providing a process for analyzing an analyte, in particular, an analyte in a biological solution, which permits thereof in a simple and cost-favorable medium, which presents the possibility of miniaturization and offers the possibility of integration in arrays, which, due to its lack of any requirement for marking of the analyte, offers a high sensitivity and specificity with respect to small analyte amounts, and which offers, as well, a high measurement throughput and a high robustness. At the same time, the present invention also provides a solution to the challenge of providing a sensor, in particular, a biosensor, for transforming the process.

The core concept of the invention resides in generating, as a result of a bonding of the analyte molecules to ligands, a variation of the force on an elastic molecule secured to a ligand, the elastic molecule being mechanically excitable, whereby this variation is optically detected in the form of a variation or difference of the fluorescence energy resonance transfer (FRET) between two chromophores in the elastic molecule. The forces occur due to the relative movement between the analyte solution and the arrangement structure to which the elastic molecule is bound and these forces effect, consequently, an analyte-dependent extension of the elastic connection between both chromophores and consequently lead to an enlargement of the spacing between the chromophores. In this connection, the system is advantageously configured to exploit the fact that the chromophores couple with one another via the elastic coupling when at a spacing to one another of approximately the Foerster radius.

The fluorescence energy resonance transfer (FRET) reacts very sensibly to this variation or difference of the spacing between the chromophores in that, in connection with enlarged spacings, only relatively few transfers between the chromophores can occur. The fluorescence radiation of the system is then emitted substantially only by the chromophore which has been subjected to excitation by external irradiation thereof, whereupon this fluorescence condition expresses itself as a variation in the relationship of the intensities of both fluorescence wavelengths. A system loaded by the analyte reacts, consequently, in a manner which is measurably different than the reaction of a system which is not so loaded by an analyte. A qualitative and, in particular, a quantitative, analysis of the analyte is consequently possible.

The system can be conceptualized such that both fluorescence wavelengths are dissimilar or are similar. In connection with dissimilar wavelengths, a synchronous intake of the wavelength intensities can be undertaken. A constellation, in which the chromophores fluoresce with time-shifted transfers at the same wavelengths, would, in particular, implicate the use of pulsed irradiation. The intake of the intensities of the correspondingly time-shifted emissions of the donor and the acceptor can be effected via a lock-in-process.

Since pursuant to the present invention fluorescent lights can be optically detected, the biosensor offers a high sensitivity for such fluorescence processes. In contrast to the conventional processes, a fluorophor marking of an analyte analyzed in accordance with the inventive process is superfluous.

As noted, the fluorescence energy resonance transfer (FRET) is exploited, this transfer occurring within certain elastic molecules, hereinafter designated as "springs". These molecules are fixedly connected with an arrangement or base structure. In this connection, the property that the springs, following an optical excitation in a predetermined frequency range, emit fluorescent light in two different other frequency ranges, is exploited, whereby the relationship of both emission intensities is strongly dependent upon—i.e., is very sensitive to—the form of the springs including, in particular, the length of the mechanical extension of the springs.

It is of particular advantage that the inventive biosensor can be miniaturized, can be arranged in arrays at a high density, and can be operated with relatively few sample analytes. An advantage in connection with the integration and miniaturization of the biosensor lies in the fact that the necessary optical and mechanical excitation of the substrate can be effected globally while it is easily possible to conduct the optical detection of the molecular reactions which are locally released. The detection is not limited to certain classes of the biomolecules, so long as the bonding results which precede the detection activity lead to a measurable difference of the forces acting on the springs. The inventive biosensor can be configured for measurements of a row of analyte concentrations arranged at intervals.

Ultimately, a row or series of different measurements can be conducted by the inventive biosensor. Thus, for example, it is possible to characterize the concentration of analyte molecules or to undertake the measurement of the kinetic forces between ligands and analyte molecules.

The inventive biosensor can be deployed in order to analyze the change effects between different change effects partners. The following can be taken into account, for example, as a pair of ligands, or respectively, analyte molecules: small molecules and macro molecules, single strand nucleic acids, and, eventually, various different hybridized single strand nucleic acids, nucleic acids, or peptides, and macromolecules. Change effects which are of interest in connection with in-vivo analysis are, for example, change effects between small molecules or proteins as ligands and membrane-capable receptors as analyte molecules.

The molecular springs are preferably configured in the following manner. A group of springs are immobilized relative to the arrangement structure by, for example, covalent chemical bonds or other conventional strong bonds such as the bonds which are known to form between a biotinyl group and streptavidin. In this connection, the springs comprise a fluorescence donor and a fluorescence receptor correspondingly configured with respect to the respective fluorescence donor. In this connection, the size of the spring, the position, and the type of both fluorophors are selected such that, in the non-tensioned or non-extended condition of the spring, there is a substantially high probability that a Foerster transfer can occur from the donor to the acceptor, as compared to the probability of such an event occurring in the extended or tensioned condition of the spring. The springs comprise an elastic portion, which can be realized as polymer molecules whose entropic elasticity is exploited or can be realized as nanotubes whose bending elasticity is exploited. At the respective end of the spring which is in opposition to the immobilization end thereof, a selective desired ligand is coupled thereto. This coupling is covalent or is realized by another strong bond. It is not necessary that both fluorophors are a portion of the spring. Additionally, a fluorophor on the foot of the spring can be connected directly to the arrangement structure.

The system has, in this connection, one or several arrangement structures to which the springs are fixed in an immobilized manner. The springs have a distance to one another on the arrangement structure which is relatively large in contrast to the spacing between the two fluorophors within a spring. If necessary, the surface of the arrangement structure is structured such that the springs are somewhat raised relative to the arrangement structure. This configuration ensures that sufficient quantities of the springs can be engaged by movement of the medium. The arrangement structures are moved by means of an apparatus which, in particular, produces a periodic relative movement between the arrangement structure and the fluid medium. It can also be advantageous to choose a transparent arrangement structure or an arrangement structure of a transparent capillary.

At the same time, a light source is deployed which is specifically tuned to effect excitation of the donors. This light excitation can, in any event, be accomplished in a pulsed manner, in order to differentiate, via a lock-in-reinforcement, over background light radiation. An optical detector detects not only the fluorescence of the donors but also the fluorescence of the acceptors. The system comprises, at the same time, a control and evaluation electronic unit which couples the fluorescence signals with a signal which corresponds to the periodic relative movement, whereupon it is possible to effect the measurement of the fluorescence value in the lock-in-process. The optical excitation can also be effected via the surface plasmons, whereby these surface plasmons are produced via light irradiation along the underside of the transparent arrangement structure. By use of surface plasmons, the fluorescence output and the signal-to-noise ratio can be increased still further. The emission of light for the optical excitation and the optical detection can be effected on various sides of the arrangement structure.

Various configurations of the sensor are possible: thus, the individual components of the sensor can be realized in different configurations. By appropriate selection, in particular, of the type of the arrangement structure and the manner by which the relative movement between the arrangement structure and the surroundings is produced, it is possible to encompass different usage fields, which comprise, without limitation, the following exemplary usage fields:

Elasto-optical biosensors integrated in microfluids:

The springs are immobilized in a light transmitting capillary, through which the analyte solution is pumped. The pumping occurs, in this regard, in a non-uniform manner—that is, in a pulsed manner. The correlation of the pulse with the fluorescence signals permits the exploitation of the lock-in process for increasing the signal-to-noise ratio. The capillary can be comprised as a portion of a complex analytical on-line system, in which other separation or analytical steps can be performed upstream or downstream of the capillary (for example, electrospray-mass spectrometry).

Elasto-optical biosensors having a quartz oscillator:

The relative movement is produced via a suitable quartz oscillator, which can be piezo-electrically excited to oscillation. In accordance with this principle, it is easy to arrange an array of sensor elements, whereby each of these elements comprises a spring having a ligand thereon different than those ligands on the other springs. Thus, in connection with a mechanical global excitation conducted in parallel and in a small space, many different ligand analyte change effects can be simultaneously measured.

Elasto-optical biosensor for in-vivo uses:

The arrangement structures on which the springs are immobilized can also be comprised of small magnetic particles. The relative movement is then produced via a high frequency or pulsed magnetic field. This technology permits measurement in-vivo. For example, the change effects between the ligands and the membrane-capable proteins on the cell surfaces in a cell culture can be examined.

BRIEF DESCRIPTION OF THE DRAWINGS

An embodiment of the present invention is described in further detail hereinafter with reference to the figures of the drawings.

DETAILED DESCRIPTION OF THE PREFERRED EMBODIMENT

Figure 1:
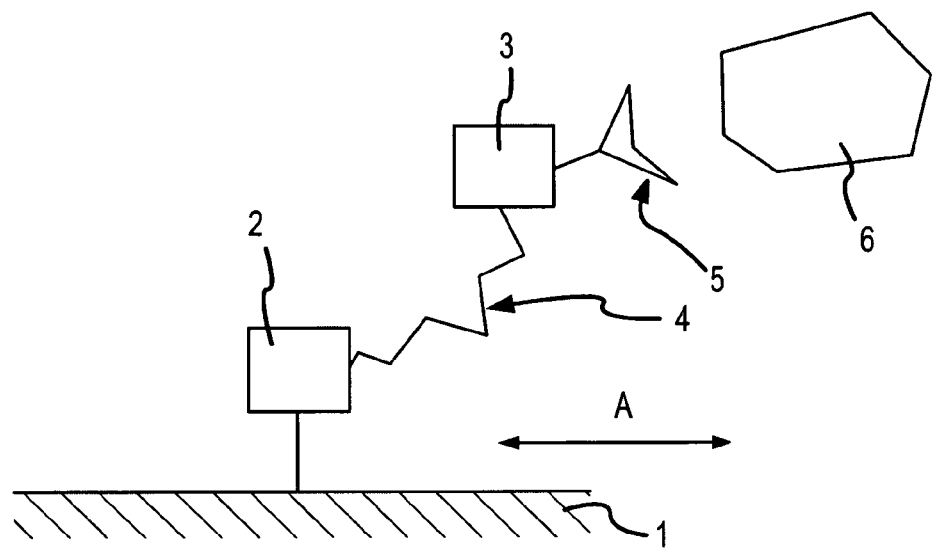
FIG. 1 is a schematic view of the operative principle of an inventive sensor.

The operative principle of the inventive sensor is schematically shown in FIG. 1. A molecular spring is secured in an immobilized manner to an arrangement structure or base 1, which is, preferably, a gold-coated arrangement structure and which is subjected to a periodic relative movement (arrow A) relative to its surroundings. The spring comprises a first fluorophor 2 and a second fluorophor 3, whereby, in this situation, the first fluorophor 2 is a fluorescence donor and the second fluorophor 3 is a correspondingly configured fluorescence acceptor. Both fluorophors are connected via an elastic element 4. A ligand 5 is coupled to the end of the spring, whose bond with an analyte molecule 6 is to be examined. It is advantageous if the arrangement structure comprises a surface structure which permits the springs to project into the analyte solution so that the springs can be engaged by movement of the fluid.

Figure 2:
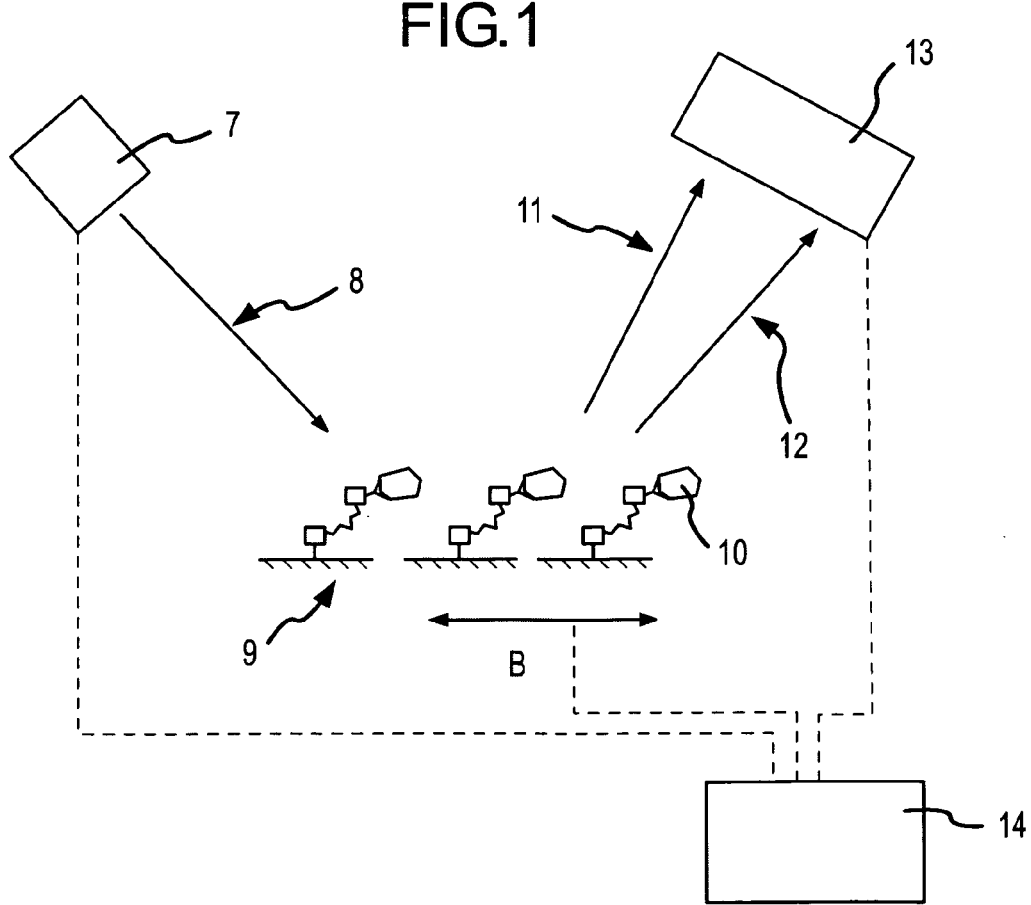
FIG. 2 is a schematic view of the measurement principle having the inventive sensor illustrated in FIG. 1.

The measurement principle of the present invention using the inventive sensor is shown in FIG. 2. A light source 7 emits light 8 of a wavelength $\lambda_1$ which effects excitation of the fluorescence donors. Depending upon the deflection of the springs 9, which occurs as a result of the relative movement (arrow B) and which is a function of the type of analyte molecule 10 connected to the ligand, a variation occurs in the relationship between the intensities of the fluorescent light 11 of the wavelength $\lambda_1$, which is directly emitted from the donor, and the fluorescent light 12 of the wavelength $\lambda_2$, which is transferred via the Foerster transfer from the donor to the acceptor and is subsequently emitted by the acceptor. The light of the wavelengths $\lambda_1$ and $\lambda_2$ is registered in a detector 13. A time-regulated pulse output of the light emission, the relative movement of the arrangement structure and its surrounding, as well as the detected light intensities, are correlated in a lock-in-amplifier 14, in order to thereby increase the signal-to-noise ratio.

A typical run through the steps of the inventive process is as follows:

Initially, the analyte is disposed together with the biosensor. Depending upon the respective configuration, the analyte is disposed on the sensor, is guided thereto by a fluid apparatus, or a portion of the sensor is configured in the analyte. It is important that the analyte encloses the springs or is wound around the springs. During an equilibrium phase, the analyte molecules have the opportunity to connect to the ligands on the ends of the springs via specific bonds. Thereafter, the analyte and the arrangement structure of the springs are set in opposed periodic movement relative to one another. In this connection, the amplitude and frequency of the movement is selected such that the forces on the springs not having any analyte molecules and the forces on the springs having bound analyte molecules are clearly different from one another and, consequently, the deflections or deviations of these differently loaded springs are clearly different.

At the same time, the fluorescence of the donor is specifically generated via irradiation of the donor by light radiation to cause excitation thereof without, however, effecting direct excitation of the acceptor via this light radiation. The excitation of the acceptor occurs, in contrast, indirectly via the Foerster transfer from the donor to the acceptor. In the event that a spring is only slightly deflected or not deflected at all, the donor and the acceptor are disposed relatively closely adjacent to one another and there is a high probability that the Foerster transfer will occur. In this connection, a high or increased fluorescence intensity is detected in the frequency range of the emission of the acceptor and a reduced intensity of the emission of the donor is detected. In the event that an analyte molecule has bonded onto the ligands, the forces (friction, loading) which are produced by virtue of the periodic movement of the spring take effect. If the force increase is sufficiently large, the spring is deflected to the extent that the spacing between the donor and the acceptor is so large as to no longer permit any Foerster transfer. In this circumstance, it is primarily the donor which will fluoresce with increased intensity while the acceptor will fluoresce with reduced intensity. The relationship of the intensities of the two fluorophors shifts, therefore, as a function of those force increases which lead to fluorescence of the donor.

The fluorescence is detected. To improve the signal-to-noise ratio, the fluorescence signal is correlated with the mechanical excitation, the movement between the spring and its surroundings, and the optical excitation of the fluorescence. The relative variations or differences of the intensities of the fluorescence from the donor and the acceptor, as compared to control references which do not comprise any specifically bound analyte molecules, permit conclusions to be drawn concerning the difference of the force on the springs, such differences resulting from the bonding of the analyte molecules, and, thus, permit conclusions to be drawn concerning the size and the type of the analyte molecules, as well as their concentration.

The specification incorporates by reference the disclosure of German priority document 102 21 792.0 filed 15 May 2002.

The present invention is, of course, in no way restricted to the specific disclosure of the specification and drawing, but also encompasses any modifications within the scope of the appended claims.

We claim:

1. A process for at least one of a qualitative analysis and a quantitative analysis of an analyte in a solution, the process comprising:

on an arrangement structure on which a first chromophore is disposed which is capable of emitting a fluorescent light of a wavelength $\lambda_1$ in response to irradiation of the first chromophore with an electro-magnetic radiation, which causes the first chromophore to absorb a wavelength $\lambda$, and the first chromophore being interconnected by an elastic coupling with a second chromophore at a spacing relative to the second chromophore such that a fluorescence resonance energy transfer (FRET) is possible between the second chromophore and the first chromophore, the second chromophore being capable of emitting a fluorescent light of a wavelength $\lambda_2$ in response to a transfer of light in a non-direct irradiation manner to the second chromophore and the second chromophore being connected to a ligand having the analyte coupled thereto, irradiating the first chromophore with an electro-magnetic radiation while simultaneously moving the arrangement structure 1 and the analyte relative to one another in a manner which effects extension of the elastic coupling interconnecting the first chromophore and the second chromophore;

measuring the intensities of the fluorescent light having the respective wavelength $\lambda_1$ and the fluorescent light having the respective wavelength $\lambda_2$ during the movement of the arrangement structure and the analyte relative to one another; and determining at least one of the type and the amount of the analyte as a function of the intensities of the fluorescent light having the respective wavelength $\lambda_1$ and the fluorescent light having the respective wavelength $\lambda_2$ which have been monitored during the movement of the arrangement structure and the analyte relative to one another.

2. A process for at least one of a qualitative analysis and a quantitative analysis of an analyte in a solution according to claim 1, wherein the first chromophore and the second chromophore have the characteristic that wavelength $\lambda_1$ of the fluorescent light emitted by the first chromophore and the respective wavelength $\lambda_2$ of the fluorescent light emitted by the second chromophore are different from one another.

3. A process for at least one of a qualitative analysis and a quantitative analysis of an analyte in a solution according to claim 1, wherein the wavelength $\lambda_1$ of the fluorescent light emitted by the first chromophore and the respective wavelength $\lambda_2$ of the fluorescent light emitted by the second chromophore are identical to one another.

4. A process for at least one of a qualitative analysis and a quantitative analysis of an analyte in a solution according to claim 1, wherein measuring the intensities of the fluorescent light having the respective wavelength $\lambda_1$ and the fluorescent light having the respective wavelength $\lambda_2$ is performed at a predetermined delay following the excitation of the first chromophore.

5. A process for at least one of a qualitative analysis and a quantitative analysis of an analyte in a solution according to claim 1, wherein the elastic coupling interconnecting the first chromophore and the second chromophore effects a significantly stronger fluorescence energy resonance transfer (FRET) in its non-extended position in comparison to its extended position.

6. A process for at least one of a qualitative analysis and a quantitative analysis of an analyte in a solution according to claim 1, wherein irradiating the first chromophore with an electro-magnetic radiation while simultaneously moving the arrangement structure and the analyte relative to one another includes moving the arrangement structure and the analyte relative to one another in a periodic movement selected such that the elastic coupling is deflected in a manner which does not result in failure of the elastic coupling and determining at least one of the type and the amount of the analyte includes determining the mass and concentration of the analyte as a function of the intensities of the fluorescent light having the respective wavelength $\lambda_1$ and the fluorescent light having the respective wavelength $\lambda_2$ which have been monitored during the movement of the arrangement structure and the analyte relative to one another in such a periodic movement.

7. A process for at least one of a qualitative analysis and a quantitative analysis of an analyte in a solution according to claim 1, wherein irradiating the first chromophore with an electro-magnetic radiation while simultaneously moving the arrangement structure and the analyte relative to one another includes moving the arrangement structure and the analyte relative to one another in a periodic movement selected such that the elastic coupling is deflected in a manner which results in failure of the elastic coupling and determining at least one of the type and the amount of the analyte includes determining at least one of the type and the amount of the analyte as a function of the intensities of the fluorescent light having the respective wavelength $\lambda_1$ and the fluorescent light having the respective wavelength $\lambda_2$ which have been monitored during the movement of the arrangement structure and the analyte relative to one another in such a periodic movement.

8. A process for at least one of a qualitative analysis and a quantitative analysis of an analyte in a solution according to claim 1, wherein irradiating the first chromophore with an electro-magnetic radiation while simultaneously moving the arrangement structure and the analyte relative to one another includes effecting the movement of the arrangement structure and the analyte relative to one another by excitation via one of an oscillation quartz, a changing magnetic field, and a periodically operating pump.

9. A process for at least one of a qualitative analysis and a quantitative analysis of an analyte in a solution according to claim 1, wherein irradiating the first chromophore with an electro-magnetic radiation while simultaneously moving the arrangement structure and the analyte relative to one another includes effecting the movement of the arrangement structure and the analyte relative to one another by excitation via a surface plasmon which has been formed via light irradiation on the underside of a transparent arrangement structure.

10. A sensing apparatus for sensing fluorescence emitted during a process performed to effect at least one of a qualitative analysis and a quantitative analysis of an analyte in a solution, the sensing apparatus comprising:

at least one elastic molecule;

at least one arrangement structure connected to the at least one elastic molecule, the at least one arrangement structure having a first chromophore disposed thereon which is capable of emitting a fluorescent light of a wavelength $\lambda_1$ in response to irradiation of the first chromophore with an electro-magnetic radiation, which causes the first chromophore to absorb a wavelength $\lambda$, the first chromophore being interconnected by an elastic coupling with a second chromophore at a spacing relative to the second chromophore such that a fluorescence resonance energy transfer (FRET) is possible between the second chromophore and the first chromophore, the second chromophore being capable of emitting a fluorescent light of a wavelength $\lambda_2$ in response to a transfer of light in a non-direct irradiation manner to the second chromophore and the second chromophore being connected to a ligand having coupled thereto an analyte molecule, at least one of the type of which and the amount of which is to be determined;

means for moving the at least one arrangement structure and the analyte molecule relative to one another in a manner which effects extension of the elastic coupling interconnecting the first chromophore and the second chromophore;

a light source for irradiating the first chromophore with an electro-magnetic radiation so as to cause the first chromophore to absorb a wavelength $\lambda$ and emit a fluorescent light of a wavelength $\lambda_1$ in response to the irradiation of the first chromophore;

an optical detector for detecting the fluorescent light having the respective wavelength $\lambda_1$ and the fluorescent light having the respective wavelength $\lambda_2$ during the movement of the at least one arrangement structure and the analyte molecule relative to one another; and a device for associating signals representative of the detected fluorescent light with a signal representative of the movement of the at least one arrangement structure and the analyte molecule relative to one another and for associating signals representative of the detected fluorescent light with a signal representative of the excitation of the first chromophore, whereby a measurement is made possible of the intensities of the fluorescent light having the respective wavelength $\lambda_1$ and the fluorescent light having the respective wavelength $\lambda_2$ which have been monitored during the movement of the at least one arrangement structure and the analyte molecule relative to one another.

11. A sensing apparatus according to claim 10, wherein the at least one arrangement structure includes a surface which permits the at least one elastic molecule to project toward the solution in which the analyte molecule is disposed such that the at least one elastic molecule is engaged by movement of the solution fluid.

12. A sensing apparatus according to claim 10, wherein the at least one arrangement structure is transparent.

13. A sensing apparatus according to claim 10, wherein the at least one arrangement structure is comprised of magnetic particles.

14. A sensing apparatus according to claim 10, wherein the at least one elastic molecule comprises a polymer.

15. A sensing apparatus according to claim 10, wherein the at least one arrangement structure is partitioned at regular intervals into fields to thereby form an array and each of the fields comprises a spring different than the springs in the other fields.

16. A sensing apparatus according to claim 15, wherein the device for associating signals is a charge coupled device and, in particular, is a charge coupled device having dedicated portions each associated with a respective one of the fields of the array, whereby a simultaneous detection of all of the fields of the array can be performed.

17. A sensing apparatus according to claim 10, wherein the ligand is comprised of a selected one of the group of organic molecules, single strand nucleic acids, double strand nucleic acids, peptides, and proteins.

18. A process for at least one of a qualitative analysis and a quantitative analysis of an analyte in a solution according to claim 6, wherein moving the arrangement structure and the analyte relative to one another in a periodic movement includes moving the arrangement structure and the analyte relative to one another in an oscillating movement.

19. A process for at least one of a qualitative analysis and a quantitative analysis of an analyte in a solution according to claim 10, wherein the device for associating signals makes possible a measurement of the intensities of the fluorescent light having the respective wavelength $\lambda_1$ and the fluorescent light having the respective wavelength $\lambda_2$ in accordance with a lock-in-process.

20. A sensing apparatus according to claim 10, wherein the at least one elastic molecule comprises a nanotube.

* * * * *